United States Patent
Ko et al.

(10) Patent No.: US 11,712,206 B2
(45) Date of Patent: Aug. 1, 2023

(54) APPARATUS AND METHOD FOR ESTIMATING BIO-INFORMATION, AND BIO-SIGNAL MEASURING SENSOR

(71) Applicant: SAMSUNG ELECTRONICS CO., LTD., Suwon-si (KR)

(72) Inventors: Byung Hoon Ko, Hwaseong-si (KR); Seung Woo Noh, Seongnam-si (KR); Jong Wook Lee, Suwon-si (KR); Jeong Eun Hwang, Suwon-si (KR); Youn Ho Kim, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 276 days.

(21) Appl. No.: 17/101,100

(22) Filed: Nov. 23, 2020

(65) Prior Publication Data

US 2021/0345973 A1    Nov. 11, 2021

(30) Foreign Application Priority Data

May 11, 2020 (KR) ........................ 10-2020-0055692

(51) Int. Cl.
*A61B 5/00* (2006.01)
*A61B 5/02* (2006.01)
(Continued)

(52) U.S. Cl.
CPC ........ *A61B 5/7278* (2013.01); *A61B 5/02007* (2013.01); *A61B 5/02108* (2013.01);
(Continued)

(58) Field of Classification Search
None
See application file for complete search history.

(56) References Cited

U.S. PATENT DOCUMENTS 9,247,884 B2   2/2016 Yuen et al.
9,289,177 B2   3/2016 Kassim et al.
(Continued)

FOREIGN PATENT DOCUMENTS

KR   10-2017-0040034 A   4/2017
KR   10-2018-0076050 A   7/2018
(Continued)

OTHER PUBLICATIONS

Nogami et al., "Multifunctional Optical Sensor Module: Integrated Optical Micro Displacement Sensor and Its Application to a Photoplethysmographic Sensor with Measuring Contact Force," (Mar. 1, 2018) 2017 International Symposium on Micro-NanoMechatronics and Human Science (MHS). (Year: 2018).*

*Primary Examiner* — Joel Lamprecht
*Assistant Examiner* — Ashish S Jasani
(74) *Attorney, Agent, or Firm* — Sughrue Mion, PLLC

(57) ABSTRACT

An apparatus for estimating bio-information, includes a sensor including a cover having a transmitting area provided at a center of the cover, and non-transmitting areas provided at both edges of the cover, a light source configured to emit light onto an object that is in contact with the cover, and a detector configured to detect a first optical signal of the emitted light that is scattered or reflected from the object after passing through the transmitting area, and a second optical signal of the emitted light that is reflected from the non-transmitting areas. The apparatus further includes a processor configured to estimate bio-information, based on the detected first optical signal and the detected second optical signal.

18 Claims, 12 Drawing Sheets

(51) Int. Cl.
*A61B 5/021* (2006.01)
*A61B 5/16* (2006.01)
*A61B 5/024* (2006.01)

(52) U.S. Cl.
CPC .......... *A61B 5/02427* (2013.01); *A61B 5/165* (2013.01); *A61B 5/6843* (2013.01); *A61B 5/681* (2013.01)

(56) References Cited

U.S. PATENT DOCUMENTS

| | | | |
|---|---|---|---|
| 9,668,656 B2 | 6/2017 | Banet et al. | |
| 2010/0253650 A1* | 10/2010 | Dietzel | G01L 1/247 |
| | | | 73/800 |
| 2012/0016245 A1* | 1/2012 | Niwa | A61B 5/02007 |
| | | | 600/476 |
| 2016/0242694 A1 | 8/2016 | Moore et al. | |
| 2016/0338602 A1 | 11/2016 | Oksala | |
| 2017/0007138 A1* | 1/2017 | Kim | A61B 5/14552 |
| 2017/0020399 A1* | 1/2017 | Shemesh | A61B 5/02416 |
| 2017/0095168 A1 | 4/2017 | Kwon et al. | |
| 2017/0251935 A1 | 9/2017 | Yuen | |
| 2018/0177413 A1 | 6/2018 | Kwon et al. | |
| 2018/0220962 A1 | 8/2018 | Palley et al. | |
| 2019/0008399 A1 | 1/2019 | Mukkamala et al. | |
| 2019/0076032 A1* | 3/2019 | Park | A61B 5/02438 |
| 2019/0216340 A1 | 7/2019 | Holz et al. | |
| 2020/0196881 A1 | 6/2020 | Zemel | |
| 2020/0214579 A1 | 7/2020 | Phillips et al. | |
| 2020/0323438 A1* | 10/2020 | Sawada | G01L 1/22 |
| 2022/0283303 A1* | 9/2022 | Kato | G01L 5/00 |

FOREIGN PATENT DOCUMENTS

| | | |
|---|---|---|
| WO | 2019/010616 A1 | 1/2019 |
| WO | 2019/051108 A1 | 3/2019 |
| WO | 2019/060671 A1 | 3/2019 |
| WO | 2019/170903 A1 | 9/2019 |

* cited by examiner

APPARATUS AND METHOD FOR ESTIMATING BIO-INFORMATION, AND BIO-SIGNAL MEASURING SENSOR

CROSS-REFERENCE TO RELATED APPLICATION

This application claims priority to Korean Patent Application No. 10-2020-0055692, filed on May 11, 2020, in the Korean Intellectual Property Office, the disclosure of which is incorporated by reference herein in its entirety.

BACKGROUND

1. Field

Example embodiments of the disclosure relates to an apparatus and method for non-invasively estimating bio-information, and a bio-signal measuring sensor.

2. Description of Related Art

Generally, methods of non-invasively measuring blood pressure without damaging a human body include a method to measure blood pressure by measuring a cuff-based pressure and a method to estimate blood pressure by measuring pulse waves without the use of a cuff.

A Korotkoff-sound method is one of cuff-based blood pressure measurement methods, in which a pressure in a cuff wound around an upper arm is increased, and blood pressure is measured by listening to the sound generated in the blood vessel through a stethoscope while the pressure is decreased. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

In accordance with an aspect of an example embodiment, there is provided an apparatus for estimating bio-information, the apparatus including a sensor including a cover having a transmitting area provided at a center of the cover, and non-transmitting areas provided at both edges of the cover, a light source configured to emit light onto an object that is in contact with the cover, and a detector configured to detect a first optical signal of the emitted light that is scattered or reflected from the object after passing through the transmitting area, and a second optical signal of the emitted light that is reflected from the non-transmitting areas. The apparatus further includes a processor configured to estimate bio-information, based on the detected first optical signal and the detected second optical signal.

The light source may be interposed between the cover and the detector.

The sensor may further include supports configured to support the cover so that the non-transmitting areas have a cantilever shape.

The detector may have a first area in which the first optical signal is detected, and a second area in which the second optical signal is detected.

The processor may be configured to divide the detector into the first area and the second area, based on a quantity of light that is detected by the detector in an initial state before a force is applied to the sensor.

The sensor may further include a light concentrator configured to concentrate the first optical signal and the second optical signal toward the detector.

The processor may be further configured to obtain a force that is applied to the object, based on an intensity of the detected second optical signal that is changed as the non-transmitting areas are deformed by a pressing force of the object on the cover.

The processor may be further configured to obtain the applied force, based on the intensity of the detected second optical signal, using a pre-defined force estimation model.

The processor may be further configured to obtain a contact pressure based on the obtained force, and estimate the bio-information, based on the obtained contact pressure and the detected first optical signal.

The processor may be further configured to guide a contact state of the object, based on the obtained force.

The bio-information may include any one or any combination of a blood pressure, a vascular age, an arterial stiffness, an aortic pressure waveform, a stress index, and a fatigue level.

In accordance with an aspect of an example embodiment, there is provided a method of estimating bio-information, the method including emitting light onto an object that is in contact with a cover having a transmitting area provided at a center of the cover, and non-transmitting areas provided at both edges of the cover, detecting a first optical signal of the emitted light that is scattered or reflected from the object after passing through the transmitting area, detecting a second optical signal of the emitted light that is reflected from the non-transmitting areas, and estimating bio-information, based on the detected first optical signal and the detected second optical signal.

The estimating of the bio-information may include obtaining a force that is applied to the object, based on an intensity of the detected second optical signal that is changed as the non-transmitting areas are deformed by a pressing force of the object on the cover.

The obtaining of the force may include obtaining the applied force, based on the intensity of the detected second optical signal, using a pre-defined force estimation model.

The estimating of the bio-information may further include obtaining a contact pressure based on the obtained force, and estimating the bio-information, based on the obtained contact pressure and the detected first optical signal.

The method may further include including guiding a contact state of the object, based on the obtained force.

In accordance with an aspect of an example embodiment, there is provided a bio-signal measuring sensor including a cover having a transmitting area provided at a center of the cover, and non-transmitting areas provided at both edges of the cover, a light source configured to emit light onto an object that is in contact with the cover, and a detector configured to detect a first optical signal of the emitted light that is scattered or reflected from the object after passing through the transmitting area, and a second optical signal of the emitted light that is reflected from the non-transmitting areas that are deformed by a contact force of the object. The light source may be interposed between the cover and the detector.

The sensor may further include supports configured to support the cover so that the non-transmitting areas have a cantilever shape and are deformed by the contact force of the object.

The sensor may further include a base that is spaced apart from the cover. The detector may be disposed on the base in an array.

The sensor may further include a light concentrator configured to concentrate the first optical signal and the second optical signal toward the detector.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
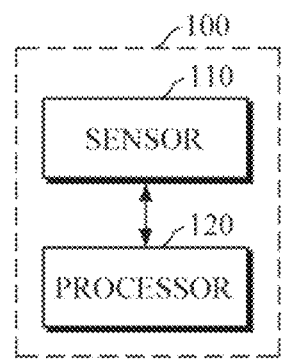
FIG. 1 is a block diagram illustrating an apparatus for estimating bio-information, according to an example embodiment.

Details of example embodiments are provided in the following detailed description and drawings. Advantages and features of embodiments, and methods of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements may not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., may be understood as a unit or device for performing at least one function or operation and may be embodied as hardware, software, or a combination thereof.

FIG. 1 is a block diagram illustrating an apparatus for estimating bio-information, according to an example embodiment. The apparatus for estimating bio-information according to embodiments may be embedded in a terminal, such as a smartphone, a tablet PC, a desktop computer, a laptop computer, and the like, or may be manufactured as an independent hardware device. In this case, if the apparatus for estimating bio-information is manufactured as an independent hardware device, the device may be a wearable device worn on an object OBJ so that a user may easily measure bio-information while carrying the device. Examples of the wearable device may include a wristwatch-type wearable device, a bracelet-type wearable device, a wristband-type wearable device, a ring-type wearable device, a glasses-type wearable device, a headband-type wearable device, or the like, but the wearable device is not limited thereto, and may be modified for various purposes, such as a fixed type device and the like used in medical institutions for measuring and analyzing bio-information.

Referring to FIG. 1, the apparatus 100 for estimating bio-information includes a sensor 110 and a processor 120.

As illustrated in FIG. 1, the sensor 110 may be electrically connected to the processor 120. The sensor 110 may measure a bio-signal from an object under the control of the processor 120, and may measure a signal related to a force applied by the object that is in contact with the sensor 110.

Figure 2A:
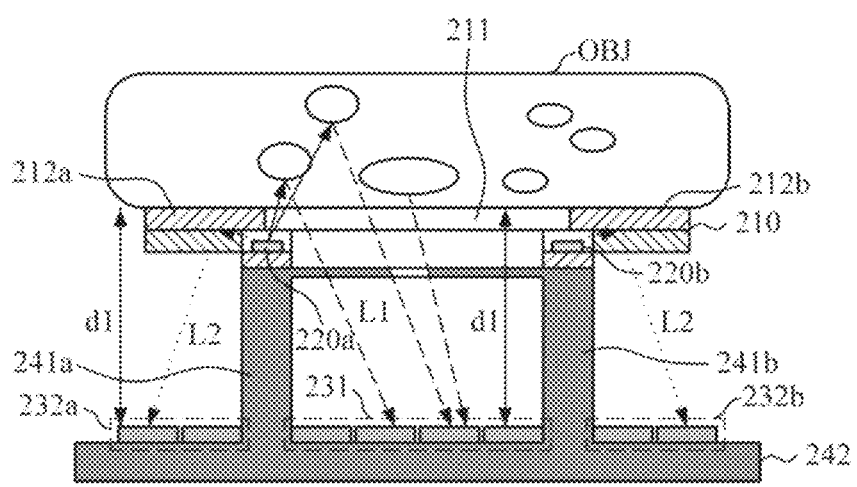
FIGS. 2A and 2B are diagrams explaining a structure of a sensor according to an example embodiment.
Figure 2B:
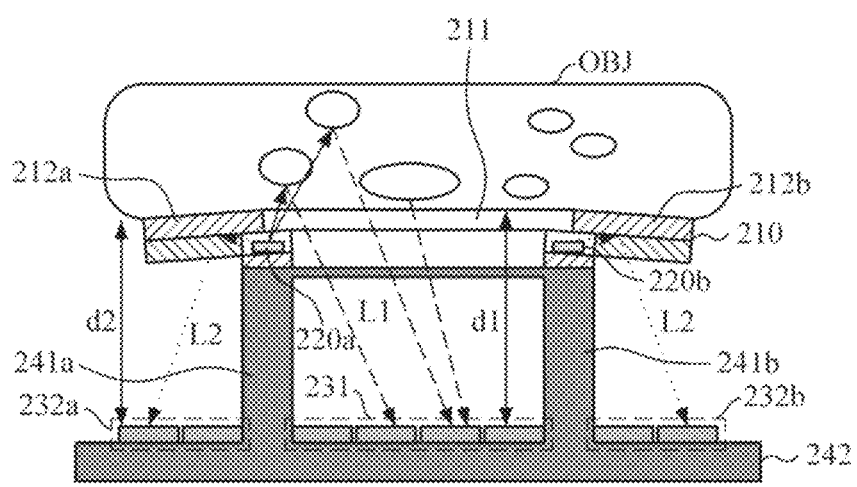

FIGS. 2A and 2B are diagrams explaining a structure of a sensor according to an example embodiment.

Referring to FIGS. 2A and 2B, the sensor 110 according to the example embodiment has a cover 210 disposed at the top thereof. The cover 210 has one smooth surface for contact with the object OBJ. The cover 210 has a transmitting area 211 formed at the center thereof and non-transmitting areas 212a and 212b formed at both edges thereof. The transmitting area 211 may be made of a transparent material, e.g., glass, to transmit light. The non-transmitting areas 212a and 212b may be made of an opaque material to prevent light transmission, or may be integrally formed with the transmitting area 211 using a transparent material, with the surface being coated with a shielding material to prevent light from penetrating thereinto.

Further, the sensor 110 includes supports 241a and 241b for supporting the cover 210. As illustrated in FIGS. 2A and 2B, a first support 241a may support a boundary between the transmitting area 211 and the first non-transmitting area 212a of the cover 210, so that the first non-transmitting area 212a may have a cantilever shape; and the second support 241b may support a boundary between the transmitting area 211 and the second non-transmitting area 212b of the cover 210.

The sensor 110 includes a base 242 that is spaced apart by a predetermined distance d1 from the cover 210. The base 242 may be a substrate. The supports 241a and 241b may be connected from the base 242.

As illustrated in FIG. 2B, the non-transmitting areas 212a and 212b are supported by the supports 241a and 241b in a cantilever shape, such that when the object OBJ in contact with the cover 210 changes a pressing force applied to the cover 210, the non-transmitting areas 212a and 212b may be deformed. That is, when the object OBJ changes a pressing force, deformation may occur, causing a distance between the non-transmitting areas 212a and 212b and the base 242 to be changed from a distance d1 before the contact is made to a distance d2 after the force is applied.

The sensor 110 includes one or more light sources 220a and 220b for emitting light onto the object OBJ when the object OBJ comes into contact with a contact surface of the cover 210. The light sources 220a and 220b may emit light of different wavelengths. The number of the light sources 220a and 220b is not limited to the illustrated example. The first light source 220a may be interposed between the first support 241a and the cover 210, and the second light source 220b may be interposed between the second support 241b and the cover 210. For example, the light sources 220a and 220b may be stacked between the bottom of the cover 210 and the supports 241a and 241b. The light sources 220a and 220b may include any one or any combination of a light emitting diode (LED), a laser diode, and a phosphor, but are not limited thereto.

Further, the sensor 110 includes detectors 231, 232a and 232b disposed on the base 242. The detectors 231, 232a and 232b may be arranged successively in a one-dimensional array or a multi-dimensional array. The detectors 231, 232a and 232b may include a photodiode, a photo transistor (PTr), an image sensor such as a complementary metal-oxide semiconductor (CMOS) image sensor or a charge-coupled device (CCD) image sensor, and the like, but are not limited thereto.

The detectors 231, 232a and 232b may be divided into a first area and a second area. The detector of the first area may detect a first optical signal (L1) of light, which is emitted by the light sources 220a and 220b and is reflected from the surface of the object OBJ after passing through the transmitting area 211 of the cover 210 or is scattered or reflected from body tissue, such as blood vessel tissue and the like, after entering into the object OBJ. The detectors 232a and 232b of the second area may detect a second optical signal L2 of light, which is emitted by each of the light sources 220a and 220b and is reflected from the non-transmitting areas 212a and 212b of the cover 210, respectively. In this case, the first area and the second area may be pre-divided based on light detected by the detectors 231, 232a and 232b in an initial state before the light sources are driven.

Figure 3:
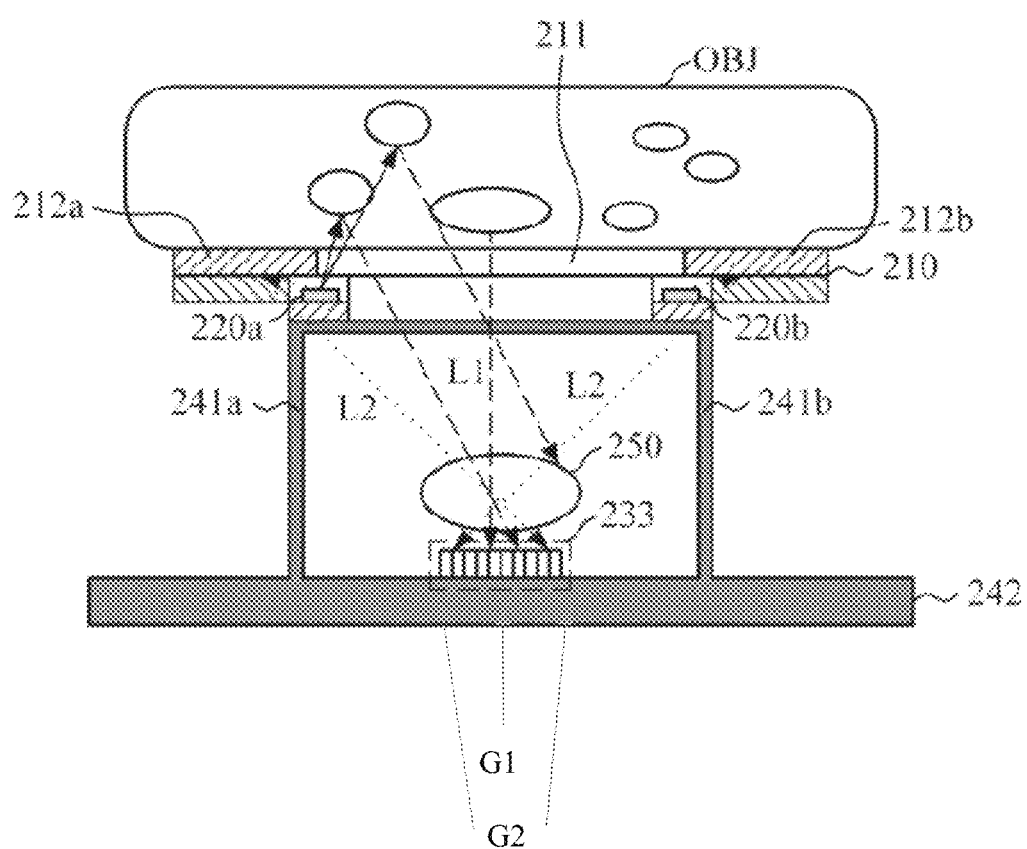
FIG. 3 is a diagram explaining a structure of a sensor according to another example embodiment.

FIG. 3 is a cross-sectional diagram of a sensor 110 to explain a structure of a sensor according to another example embodiment.

Referring to FIG. 3, the sensor 110 according to the other example embodiment includes a detector 233 that has a small size and is disposed at the center of the base 242. Further, the sensor 110 may further include a light concentrator 250 for concentrating the first optical signal of light, which is emitted by the light sources 220a and 220b and is scattered or reflected from the object after passing through the transmitting area 211, and the second optical signal of light, which is reflected from the non-transmitting areas 212a and 212b, toward the detector 233. In this case, the light concentrator 250 may include a lens. As described above, according to an initial setting, the detector 233 may be divided into a first area or first group G1 for detecting the first optical signal and a second area or group G2 for detecting the second optical signal. The processor 120 may estimate a contact force based on the second optical signal detected in the second area, and may estimate bio-information based on the estimated contact force and the first optical signal, as described above.

Figure 4A:
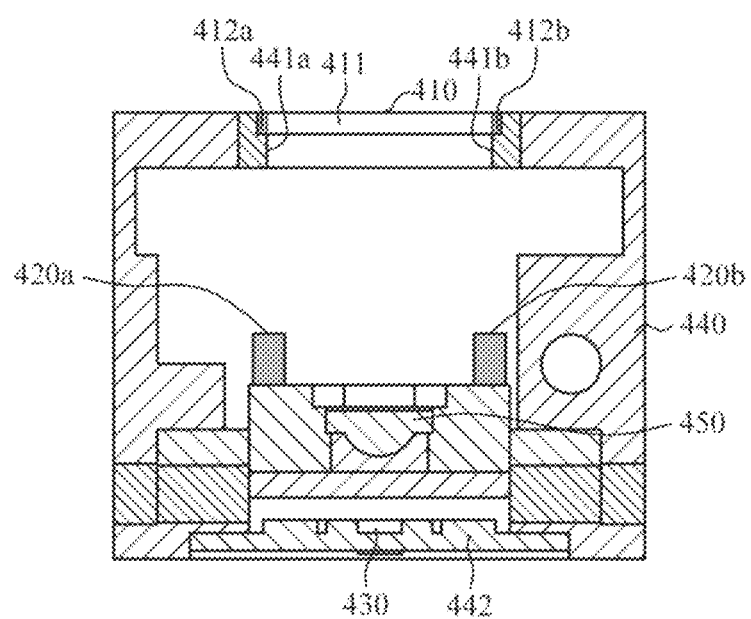
FIGS. 4A, 4B and 4C are diagrams explaining a structure of a sensor according to yet another example embodiment.
Figure 4B:
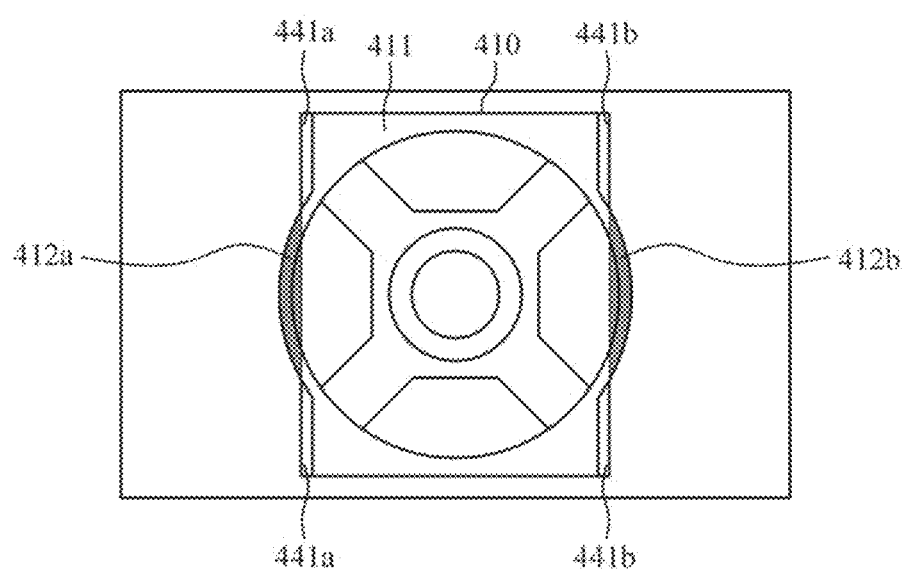
Figure 4C:
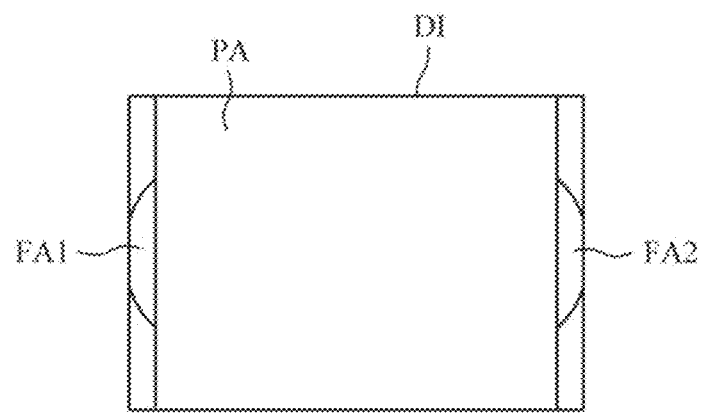

FIGS. 4A, 4B and 4C are diagrams explaining a structure of a sensor according to yet another example embodiment. FIG. 4A illustrates a cross-sectional diagram of the sensor 110 when viewed from the front, and FIG. 4B illustrates a cross-sectional diagram of the sensor 110 when viewed from the top.

Referring to FIGS. 4A, 4B, and 4C, the sensor 110 has a cover 410 disposed at the top thereof, which comes into contact with the object OBJ. The cover 410 has one smooth surface for contact with the object OBJ. The cover 410 has a transmitting area 411 formed at the center thereof and non-transmitting areas 412a and 412b formed at both edges thereof. As described above, the transmitting area 411 may be made of a transparent material, e.g., glass, to transmit light. The non-transmitting areas 412a and 412b may be made with an opaque reflective surface to reflect light, or may be integrally formed with the transmitting area 211 using a transparent material, with the surface being coated with a reflective material to prevent light from penetrating thereinto.

Further, the sensor 110 may have supports 441a and 441b for supporting the cover 410. The supports 441a and 441b may be formed in a stepped shape, so that when the cover 410 is mounted on a housing 440, the supports 441a and 441b may support both sides of the cover 410. In this case, as illustrated in FIG. 4B, the stepped parts of the supports 441a and 441b are formed only at portions other than the portion where the non-transmitting areas 412a and 412b are formed, so that when the object presses the cover 410, the non-transmitting areas 412a and 412b may be deformed by the pressing force.

In addition, the sensor 110 may have a base 442 that is formed at a lower portion of the housing 440 and is spaced apart by a predetermined distance from the cover 410. The base 442 may be a substrate.

The sensor 110 includes one or more light sources 420a and 420b for emitting light onto the object OBJ when the object OBJ comes into contact with a contact surface of the cover 410. The number of the light sources 420a and 420b is not specifically limited, and the light sources 420a and 420b may emit light of different wavelengths. The sensor 110 includes a detector 430 disposed on the base 442. The detector 430 may be arranged in a one-dimensional array or a multi-dimensional array, and may include a photodiode, a photo transistor (PTr), an image sensor such as a complementary metal-oxide semiconductor (CMOS) image sensor or a charge-coupled device (CCD) image sensor, and the like, but is not limited thereto.

For example, as illustrated in FIG. 4C, an image data DI detected by the detector 430 may be divided into a first area PA for measuring a bio-signal and second areas FA1 and FA2 for measuring a contact force of the object. The first area PA may be used for detecting a first optical signal of light, which is emitted by the light sources 440a and 440b and is reflected from the surface of the object OBJ after passing through a transmitting area 411 of the cover 410 or is scattered or reflected from body tissue, such as blood vessel tissue and the like, after entering into the object OBJ. The second areas FA1 and FA2 may be used for detecting a second optical signal of light, which is emitted by each of the light sources 420a and 420b and is reflected from the non-transmitting areas 412a and 412b of the cover 410, respectively.

Further, the sensor 110 may further include a light concentrator 450 for concentrating the first optical signal of light, which is emitted by the light sources 420a and 420b and is scattered or reflected from the object after passing through the transmitting area 411, and the second optical signal of light, which is reflected from the non-transmitting areas 412a and 412b, toward the detector 430. In this case, the light concentrator 450 may include a lens.

The processor 120 may be electrically connected to the sensor 110 and may control the operation of the sensor 110. The processor 120 may estimate bio-information based on the optical signal received from the sensor 110. In this case, bio-information may include one or more of blood pressure, vascular age, arterial stiffness, aortic pressure waveform, stress index, and fatigue level.

Hereinafter, an example of estimating bio-information will be described with reference to FIGS. 2A, 2B, 5A and 5B for convenience of explanation. The same is also applied to the structure of the sensor illustrated in FIGS. 3 to 4C.

The processor 120 may obtain a contact force between the object and the cover 210 based on the second optical signal reflected from the non-transmitting areas 212*a* and 212*b*. Further, the processor 120 may estimate bio-information based on the obtained force and the first optical signal.

The processor 120 may obtain the contact force between the object and the cover 210 based on the second optical signal, and may estimate bio-information based on the obtained contact force and the first optical signal.

For example, when the object, which is in contact with the cover 210, changes a pressing force, the non-transmitting areas 212*a* and 212*b* are deformed, causing a distance between the non-transmitting areas 212*a* and 212*b* and the detectors 232*a* and 232*b* to be changed from d1 to d2, as illustrated in FIGS. 2A and 2B. The change in the distance between the non-transmitting areas 212*a* and 212*b* and the detectors 232*a* and 232*b* may directly affect a light path. A light intensity is inversely proportional to the square of the distance, and thus, by using the characteristics that the intensity of the second optical signal, received by the detectors 232*a* and 232*b* of the second area, is changed as the non-transmitting areas 212*a* and 212*b* are deformed, the processor 120 may obtain the force applied by the object to the cover 210.

For example, the processor 120 may estimate a force from the second optical signal by using a contact force estimation model that defines a correlation between the intensity of the second optical signal, which is received by the detectors 232*a* and 232*b* of the second area, and the force. The processor 120 may obtain the force by using a statistical value (e.g., mean value) of the intensity of the second optical signal, reflected by the first non-transmitting area 212*a*, and the intensity of the second optical signal reflected by the first non-transmitting area 212*b*.

Upon obtaining the contact force during a period of time when the first optical signal is measured, the processor 120 may obtain contact pressure based on an area of the cover 210, and may estimate blood pressure using oscillometry based on the obtained contact pressure at each time and the first optical signal.

Figure 5A:
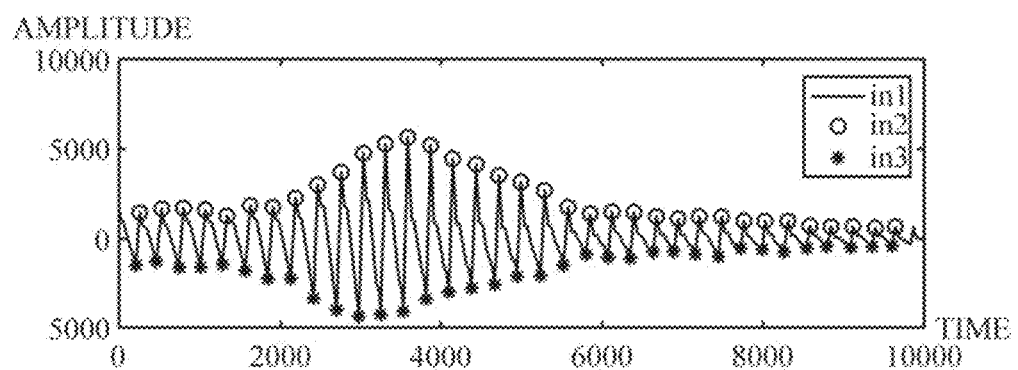
FIGS. 5A and 5B are diagrams explaining an example of estimating bio-information, according to an example embodiment.
Figure 5B:
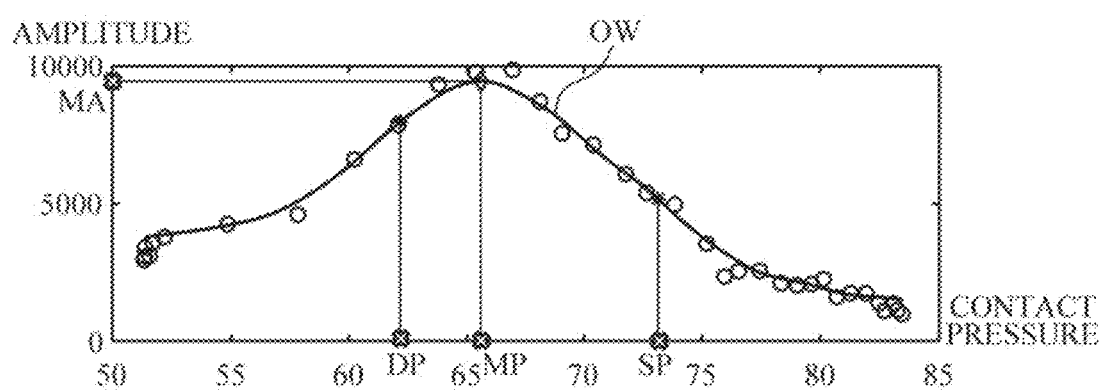

FIGS. 5A and 5B are diagrams explaining an example of estimating bio-information, according to an example embodiment.

FIG. 5A is a diagram illustrating a first optical signal measured by the detector 231 of the first area when a user gradually increases a force while touching the cover 210 of the sensor 110 with an object. FIG. 5B is a diagram illustrating an oscillometric waveform envelope obtained based on the first optical signal and contact pressure. For example, the processor 120 may extract a peak-to-peak point by subtracting a negative (−) amplitude value in3 from a positive (+) amplitude value in2 of a waveform envelope in1 at each measurement time, and may obtain the oscillometric waveform envelope OW by plotting the peak-to-peak amplitude at each measurement time against the contact pressure value at the corresponding point in time, as illustrated in FIG. 5B.

The processor 120 may obtain features for estimating blood pressure from the obtained oscillometric waveform envelope OW. For example, the processor 120 may obtain, as features for estimating blood pressure, an amplitude value MA at a maximum peak point, a contact pressure value MP at the maximum peak point, contact pressure values SP and DP at the left and right points corresponding to amplitude values having a preset ratio (e.g., 0.5 to 0.7) to the amplitude value MA at the maximum peak point, and the like from the oscillometric waveform envelope OW. However, the features are not limited thereto, and by analyzing the waveform of the first optical signal, the processor 120 may obtain additional features, such as a maximum amplitude value, a time value corresponding to the maximum amplitude value, time and amplitude values at points related to a progressive wave and a reflection wave, a combination of the obtained values, and the like.

Upon extracting the features, the processor 120 may estimate bio-information by applying a pre-defined bio-information estimation model. The bio-information estimation model may be defined as various linear or non-linear combination functions, such as addition, subtraction, division, multiplication, logarithmic value, regression equation, and the like, with no specific limitation.

Further, the processor 120 may guide a contact state of the object based on the second optical signal. For example, the processor 120 may determine a contact state, such as a contact position and the like, based on a difference between the intensity of the second optical signal, reflected by the first non-transmitting area 212*a*, and the intensity of the second optical signal reflected by the second non-transmitting area 212*b*.

For example, if a difference between the intensity of the second optical signal, reflected by the first non-transmitting area 212*a*, and the intensity of the second optical signal reflected by the second non-transmitting area 212*b* falls outside a predetermined threshold, the processor 120 may determine that a contact state is not good, and may visually guide a user so that the center of the object (e.g., center of a fingerprint) may be located at the center of the transmitting area 211.

In another example, if a difference between the intensity of the second optical signal, reflected by the first non-transmitting area 212*a*, and the intensity of the second optical signal reflected by the second non-transmitting area 212*b* falls within a predetermined threshold, the processor 120 may visually display a force, which is estimated in real time according to elapsed time, and a force to be applied according to pre-defined criteria.

Figure 6:
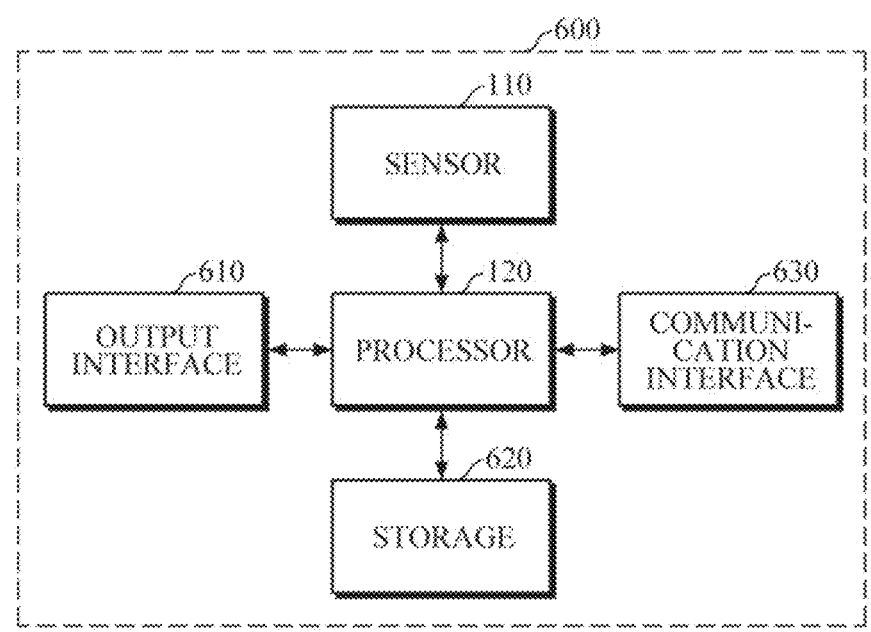
FIG. 6 is a block diagram illustrating an apparatus for estimating bio-information, according to another example embodiment.

FIG. 6 is a block diagram illustrating an apparatus for estimating bio-information, according to another example embodiment.

Referring to FIG. 6, the apparatus 600 for estimating bio-information includes the sensor 110, the processor 120, an output interface 610, a storage 620, and a communication interface 630. The sensor 110 and the processor 120 are described above with reference to FIGS. 1 to 5B, such that a detailed description thereof will be omitted.

The output interface 610 may output the first optical signal and the second optical signal, which are acquired by the sensor 110, and various processing results of the processor 120. For example, the output interface 610 may visually output an estimated bio-information value and/or guide information by using a display. Alternatively, the output interface 610 may output the information in a non-visual manner by voice, vibrations, tactile sensation, and the like, by using a speaker, a haptic device, or the like. The output interface 610 may divide a display area into two or more areas, in which the output interface 610 may output the first optical signal, the contact force and/or contact pressure, which are used for estimating bio-information, in the form of graphs in a first area; and may output an estimated bio-information value in a second area. In this case, if an estimated bio-information value falls outside a normal range, the output interface 610 may output warning information in various manners, such as highlighting an abnormal value in red and the like, displaying the abnormal value along with a normal range, outputting a voice warning message, adjusting a vibration intensity, and the like.

The storage 620 may store the first optical signal, the second optical signal and the contact force, which are obtained by the sensor 110, and/or processing results of the processor 120. Further, the storage 620 may store a variety of reference information for estimating bio-information. For example, the reference information may include user characteristics including a user's age, sex, health condition, and the like. Further, the reference information may include a bio-information estimation model, a force estimation model, a reference force, and the like, but is not limited thereto.

In this case, the storage 620 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 630 may communicate with an external device by using wired or wireless communication techniques under the control of the processor 120, and may transmit and receive various data to and from the external device. For example, the communication interface 630 may transmit a bio-information estimation result to the external device, and may receive, from the external device, a variety of reference information for estimating bio-information. In this case, the external device may include a cuff manometer, and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is an example and is not intended to be limiting.

Figure 7:
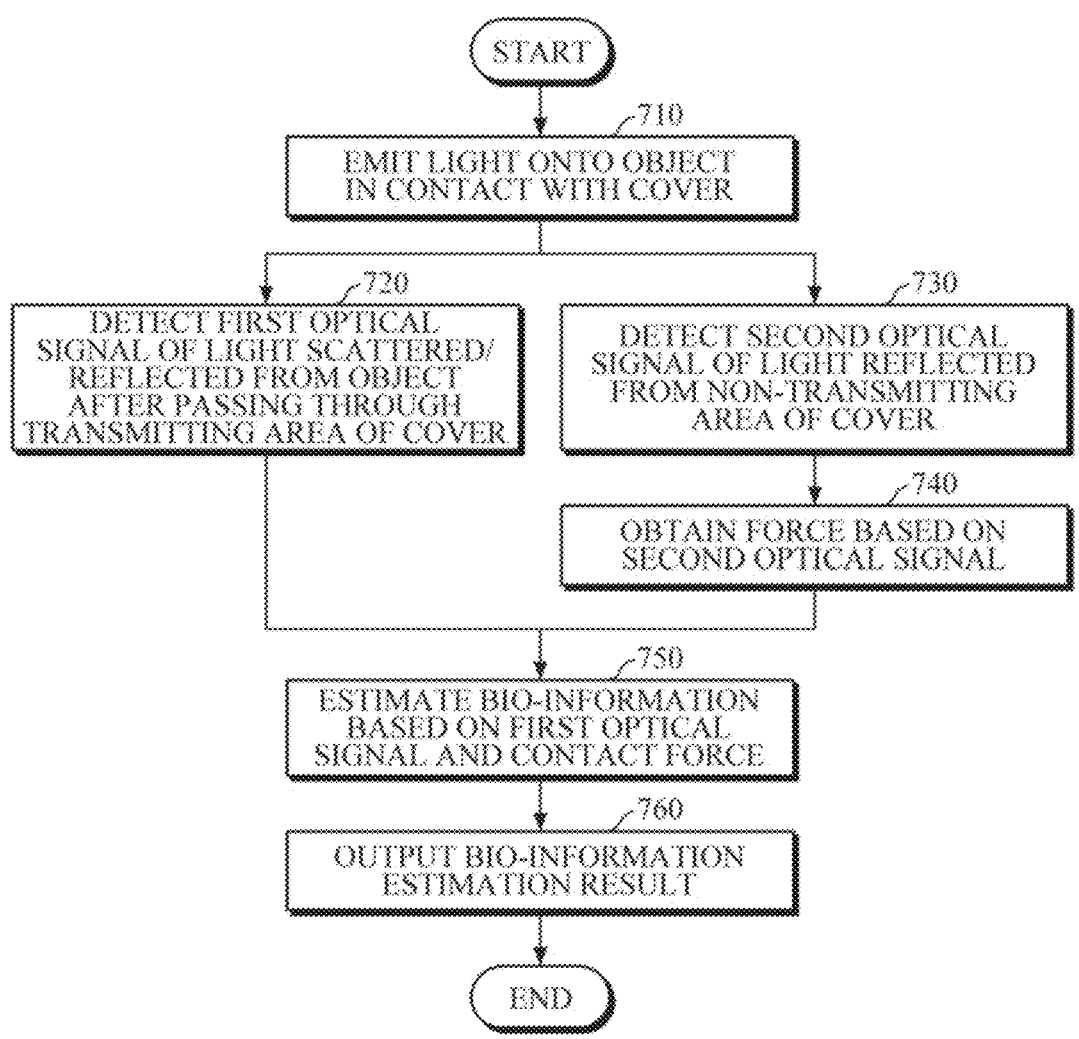
FIG. 7 is a flowchart illustrating a method of estimating bio-information, according to an example embodiment

FIG. 7 is a flowchart illustrating a method of estimating bio-information, according to an example embodiment. The method of FIG. 7 is an example of a method of estimating bio-information that is performed by the aforementioned apparatuses 100 and 600 for estimating bio-information, and will be briefly described below.

The apparatuses 100 and 600 for estimating bio-information may emit light onto an object, which is in contact with a cover, by driving light sources in operation 710. In this case, the cover has a transmitting area formed at the center thereof and non-transmitting areas formed at both edges thereof. One or more light sources may be interposed between the cover and a detector.

Then, by using a detector, the apparatuses 100 and 600 for estimating bio-information may detect a first optical signal of light in operation 720, which is emitted by the light sources and is scattered or reflected from the object after passing through the transmitting area of the cover, and may detect a second optical signal of light in operation 730, which is emitted by the light sources and is reflected from the non-transmitting areas of the cover. In this case, the detector may be divided into a first area for detecting the first optical signal by detecting light in an initial state before the light sources are driven, and a second area for detecting the second optical signal.

Subsequently, the apparatuses 100 and 600 for estimating bio-information may obtain a force, applied when the object comes into contact with the cover, based on the second optical signal in operation 740. For example, the non-transmitting areas of the cover are supported by the supports in a cantilever shape, such that the non-transmitting areas may be deformed by the contact force of the object. When the non-transmitting areas of the cover are deformed by the contact force of the object, the intensity of the second optical signal, detected in the second area of the detector, is changed. Accordingly, by using a force estimation model that defines a correlation between the change in the intensity of the second optical signal and the contact force, the apparatuses 100 and 600 for estimating bio-information may estimate a force of the object.

Next, the apparatuses 100 and 600 for estimating bio-information may estimate bio-information in operation 750 based on the first optical signal, obtained in operation 720, and the contact force obtained in operation 740. For example, the apparatuses 100 and 600 for estimating bio-information may obtain contact pressure of the object by using an area of the cover and the obtained force, and may estimate blood pressure using oscillometry based on the obtained contact pressure and an amplitude of the first optical signal.

Then, the apparatuses 100 and 600 for estimating bio-information may output a bio-information estimation result in operation 760. The apparatuses 100 and 600 for estimating bio-information may visually/non-visually output a bio-information estimation result, a bio-information estimation history, warning information and the like by using various output devices such as a display, a speaker, a haptic device and the like.

Figure 8:
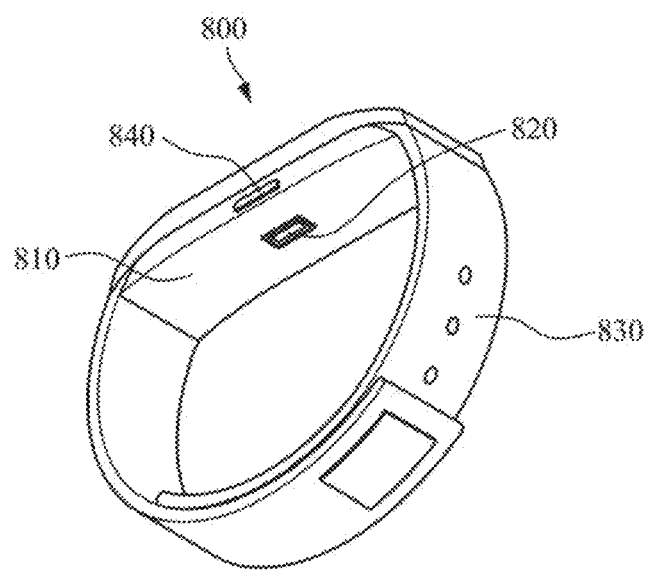
FIG. 8 is a diagram illustrating a wearable device according to an example embodiment.

FIG. 8 is a diagram illustrating a wearable device according to an example embodiment. The aforementioned example embodiments of the apparatuses 100 and 600 for estimating bio-information may be mounted in a smart watch worn on a wrist as illustrated in FIG. 8, or a smart band-type wearable device, but are not limited thereto.

Referring to FIG. 8, a wearable device 800 includes a main body 810 and a strap 830.

The main body 810 may be formed to have various shapes, and may include devices that are mounted inside or outside of the main body 810 to perform the aforementioned function of estimating bio-information and various other functions. A battery may be embedded in the main body 810 or the strap 830 to supply power to various devices of the wearable device 800.

The strap 830 may be connected to the main body 810. The strap 830 may be flexible to be bent around a user's wrist. The strap 830 may be bent in a manner that allows the strap 830 to be detached from the user's wrist or may be formed as a band that is not detachable. Air may be injected into the strap 830 or an airbag may be included in the strap 830, so that the strap 830 may have elasticity according to a change in pressure applied to the wrist, and the strap 830 may transmit the change in pressure of the wrist to the main body 810.

The main body 810 may include a sensor 820 for measuring a bio-signal. The sensor 820 may be mounted on a rear surface of the main body 810, which comes into contact with the upper portion of a user's wrist, as illustrated in FIG. 8. However, the sensor 820 is not limited thereto, and may be integrally formed with a manipulator 840 to function as the manipulator 840 and the sensor 820.

The manipulator 840 may be disposed on a lateral surface of the main body 810, and may receive a user's control instruction and transmit the received control instruction to the processor. The manipulator 840 may include a power button to input an instruction to turn on/off the wearable device 800.

A processor may be mounted in the main body 810. The processor may be electrically connected to various devices, mounted in the wearable device 800, to control operations thereof. Further, the processor may estimate bio-information by using signals measured by the sensor 820, as described above.

In addition, the main body 810 may include a storage that stores processing results of the processor and a variety of information. In this case, the variety of information may include reference information related to estimating bio-information, as well as information associated with functions of the wearable device 800.

A display may be mounted on a front surface of the main body 810, and may include a touch panel for receiving a touch input. The display may receive a touch input from a user, may transmit the received touch input to the processor, and may display a processing result of the processor. For example, the display may display an estimated bio-information value and warning/alarm information.

Moreover, a communication interface, provided for communication with an external device such as a user's mobile terminal, may be mounted in the main body 810. The communication interface may transmit a bio-information estimation result to an external device, e.g., a user's smartphone, to display the result to the user. However, the communication interface is not limited thereto, and may transmit and receive a variety of information.

The embodiments can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer readable recording medium can be distributed over a plurality of computer systems connected to a network so that a computer-readable code is written thereto and executed therefrom in a decentralized manner. Functional programs, codes, and code segments for realizing the embodiments can be easily deduced by programmers of ordinary skill in the art, to which the embodiments pertain.

It will be understood by those skilled in the art that various changes and modifications can be made without changing technical ideas and features of the disclosure. Thus, it is clear that the above-described embodiments are illustrative in all aspects and are not intended to limit the disclosure.

What is claimed is:

1. An apparatus for estimating bio-information, the apparatus comprising:
a sensor comprising:
a cover having a transmitting area provided at a center of the cover, and non-transmitting areas provided at both edges of the cover;
a light source configured to emit light onto an object that is in contact with the cover; and
one or more detectors configured as a first group of detectors to detect a first optical signal of the emitted light that is scattered or reflected from the object after passing through the transmitting area, and configured as a second group of detectors to detect a second optical signal of the emitted light that is reflected from the non-transmitting areas;
a processor configured to estimate bio-information, based on the detected first optical signal and the detected second optical signal; and
an additional light source, wherein the light source and the additional light source are disposed inside the cover, and positioned on opposite sides of the cover, and each adjacent to an opposing wall of the cover,
wherein the first optical signal from the first group of detectors represents bio-signals of the object, and the second optical signal from the second group of detectors represents contact force of the object against the sensor.

2. The apparatus of claim 1, wherein the light source is interposed between the cover and the detector.

3. The apparatus of claim 1, wherein the sensor further comprises supports configured to support the cover so that the non-transmitting areas have a cantilever shape.

4. The apparatus of claim 1, wherein the sensor further comprises a light concentrator configured to concentrate the first optical signal and the second optical signal toward the detector.

5. The apparatus of claim 1, wherein the processor is further configured to obtain a force that is applied to the object, based on an intensity of the detected second optical signal that is changed as the non-transmitting areas are deformed by a pressing force of the object on the cover.

6. The apparatus of claim 5, wherein the processor is further configured to obtain the applied force, based on the intensity of the detected second optical signal, using a pre-defined force estimation model.

7. The apparatus of claim 5, wherein the processor is further configured to obtain a contact pressure based on the obtained force, and estimate the bio-information, based on the obtained contact pressure and the detected first optical signal.

8. The apparatus of claim 5, wherein the processor is further configured to guide a contact state of the object, based on the obtained force.

9. The apparatus of claim 1, wherein the bio-information comprises any one or any combination of a blood pressure, a vascular age, an arterial stiffness, an aortic pressure waveform, a stress index, and a fatigue level.

10. A method of estimating bio-information using a sensor, the method comprising:
emitting light onto an object that is in contact with a cover having a transmitting area provided at a center of the cover, and non-transmitting areas provided at both edges of the cover;
detecting a first optical signal of the emitted light that is scattered or reflected from the object after passing through the transmitting area using one or more detectors;
detecting a second optical signal of the emitted light that is reflected from the non-transmitting areas; and
estimating bio-information, based on the detected first optical signal and the detected second optical signal,
wherein the emitting light includes emitting light from a light source and an additional light source, wherein the light source and the additional light source are disposed inside the cover, and positioned on opposite sides of the cover, and each adjacent to an opposing wall of the cover, wherein the first optical signal from a first group of detectors represents bio-signals of the object, and the second optical signal from a second group of detectors represents contact force of the object against the sensor.

11. The method of claim 10, wherein the estimating of the bio-information comprises obtaining a force that is applied to the object, based on an intensity of the detected second optical signal that is changed as the non-transmitting areas are deformed by a pressing force of the object on the cover.

12. The method of claim 11, wherein the obtaining of the force comprises obtaining the applied force, based on the intensity of the detected second optical signal, using a pre-defined force estimation model.

13. The method of claim 11, wherein the estimating of the bio-information further comprises obtaining a contact pressure based on the obtained force, and estimating the bio-information, based on the obtained contact pressure and the detected first optical signal.

14. The method of claim 11, further comprising guiding a contact state of the object, based on the obtained force.

15. A bio-signal measuring sensor comprising:
a cover having a transmitting area provided at a center of the cover, and non-transmitting areas provided at both edges of the cover;
a light source configured to emit light onto an object that is in contact with the cover; and
a one or more detectors configured as a first group to detect a first optical signal of the emitted light that is scattered or reflected from the object after passing through the transmitting area, and configured as a second group to detect a second optical signal of the emitted light that is reflected from the non-transmitting areas that are deformed by a contact force of the object, wherein the light source is interposed between the cover and the detector, and further including an additional light source, wherein the light source and the additional light source are disposed inside the cover, and positioned on opposite sides of the cover, and each adjacent to an opposing wall of the cover, and wherein the first optical signal from the first group of detectors represents bio-signals of the object, and the second optical signal from the second group of detectors represents contact force of the object against the sensor.

16. The bio-signal measuring sensor of claim 15, further comprising supports configured to support the cover so that the non-transmitting areas have a cantilever shape and are deformed by the contact force of the object.

17. The bio-signal measuring sensor of claim 15, further comprising a base that is spaced apart from the cover,
wherein the detector is disposed on the base in an array.

18. The bio-signal measuring sensor of claim 15, further comprising a light concentrator configured to concentrate the first optical signal and the second optical signal toward the detector.

* * * * *